US 12,210,082 B2

(12) United States Patent
Weiss

(10) Patent No.: US 12,210,082 B2
(45) Date of Patent: Jan. 28, 2025

(54) SCAN SEQUENCING IN MAGNETIC RESONANCE IMAGING

(71) Applicant: KONINKLIJKE PHILIPS N.V., Eindhoven (NL)

(72) Inventor: Steffen Weiss, Hamburg (DE)

(73) Assignee: Koninklijke Philips N.V., Eindhoven (NL)

(*) Notice: Subject to any disclaimer, the term of this patent is extended or adjusted under 35 U.S.C. 154(b) by 120 days.

(21) Appl. No.: 18/027,948

(22) PCT Filed: Sep. 17, 2021

(86) PCT No.: PCT/EP2021/075572
§ 371 (c)(1),
(2) Date: Mar. 23, 2023

(87) PCT Pub. No.: WO2022/063690
PCT Pub. Date: Mar. 31, 2022

(65) Prior Publication Data
US 2023/0408615 A1  Dec. 21, 2023

(30) Foreign Application Priority Data
Sep. 28, 2020 (EP) .................................... 20198626

(51) Int. Cl.
*G01R 33/56* (2006.01)
*A61B 5/00* (2006.01)
(Continued)

(52) U.S. Cl.
CPC ............ *G01R 33/567* (2013.01); *A61B 5/055* (2013.01); *A61B 5/4809* (2013.01); *G01R 33/543* (2013.01)

(58) Field of Classification Search
CPC ................ G01R 33/567; G01R 33/543; G01R 33/56509; A61B 5/055; A61B 5/4809;
(Continued)

(56) References Cited

U.S. PATENT DOCUMENTS

2009/0216108 A1  8/2009  Barrera et al.
2010/0152568 A1  6/2010  Kokubun
2016/0367166 A1* 12/2016  Piron ................. A61B 5/031

FOREIGN PATENT DOCUMENTS

CN    104667407 A    6/2015
CN    111643084 A    9/2020
(Continued)

OTHER PUBLICATIONS

"Your Child is Having an MRI Scan under Oral Sedation" Great Ormond Street Hospital for Children—website downloaded Feb. 23, 2023.
(Continued)

*Primary Examiner* — G. M. A Hyder

(57) ABSTRACT

There is provided a control system (126) for a magnetic resonance imaging system (100). The control system comprises a control module (250) configured to control the magnetic resonance imaging system to perform an examination comprising multiple scans. The control system further comprises a monitor module (252) configured to monitor a sleep state of a patient on the basis of sensor data received from a patient state sensing system (102) of the magnetic resonance imaging system. The control system further comprises a sequencing module (254) configured dynamically to determine at least part of a sequence in which the control module is to control the magnetic resonance imaging system to perform the scans, the determination being made according to the monitored sleep state of the patient and according to a sleep-appropriateness score asso-
(Continued)

ciated with one or more of the scans. A corresponding method is also provided.

16 Claims, 2 Drawing Sheets

(51) Int. Cl.
*A61B 5/055* (2006.01)
*G01R 33/54* (2006.01)
*G01R 33/567* (2006.01)

(58) Field of Classification Search
CPC ......... A61B 5/024; A61B 5/0816; A61B 5/11; A61B 5/1103; A61B 5/7285; A61B 5/721; A61B 5/4812
See application file for complete search history.

(56) References Cited

FOREIGN PATENT DOCUMENTS

| | | |
|---|---|---|
| EP | 3575812 A1 | 12/2019 |
| JP | 2008093098 A | 4/2008 |
| JP | 2011161033 A | 8/2011 |
| WO | 2016011645 A1 | 1/2016 |

OTHER PUBLICATIONS

"Your Child is Having an MRI Scan using feed and wrap' Technique" Great Ormond Street Hospital for Children—website downloaded Feb. 23, 2023.

International Search Report and Written Opinion from PCT/EP2021/075572 mailed Nov. 30, 2021.

Kramer et al Standardized Cardiovascular Magnetic Resonance Imaging (CMR) Protocols: 2020 update—Journal of Cardiovascular Magnetic Resonance, 2020.

* cited by examiner

SCAN SEQUENCING IN MAGNETIC RESONANCE IMAGING

CROSS REFERENCE TO RELATED APPLICATIONS

This application is a U.S. national phase application of International Application No. PCT/EP2021/075572 filed on Sep. 17, 2021, which claims the benefit of EP application No. 20198626.2 filed on Sep. 28, 2020 and is incorporated herein by reference.

FIELD OF THE INVENTION

The invention relates to scan sequencing in magnetic resonance imaging, in particular to a control system and control method for a magnetic resonance imaging system.

BACKGROUND OF THE INVENTION

Patient motion is the most important source of image artifacts in magnetic resonance imaging (MM). It often leads to the missing of small lesions, obscuring of important structures, or generally bad image quality, such that many scans have to be repeated. Various approaches to address patient motion have been proposed. A first approach makes use of data provided by external sensors or the MR data itself to detect motion and thereby to choose not to acquire or to discard the fraction of MR data that may otherwise introduce artifacts. This approach generally increases scan time. A second approach seeks to minimize patient motion by convenient positioning, immobilization, or patient coaching. In some pediatric imaging cases, even sedation is considered as a last resort to avoid patient motion, with obvious additional effort and side effects.

SUMMARY OF THE INVENTION

There is a need for technology that effectively avoids or addresses patient motion in an autonomous setting with minimal staff intervention.

This need is met by the subject-matter of the independent claims. Optional features are provided by the dependent claims and by the following description.

According to a first aspect, there is provided a control system for a magnetic resonance imaging system. The control system may comprise a control module configured to control the magnetic resonance imaging system to perform an examination comprising multiple scans. The control system may further comprise a monitor module configured to monitor a sleep state of a patient on the basis of sensor data received from a patient state sensing system of the magnetic resonance imaging system. The control system may further comprise a sequencing module configured dynamically to determine at least part of a sequence in which the control module is to control the magnetic resonance imaging system to perform the scans. The determination may be made according to the monitored sleep state of the patient and according to a sleep-appropriateness score associated with one or more of the scans.

In this way, sleep in the patient is supported and utilized to reduce imaging artifacts and save imaging time, thus providing improved cost-effectiveness, based on the insight that sleep solves the motion problem effectively and conveniently for the patient.

According to a second aspect, there is provided a computer-implemented method of controlling a magnetic resonance imaging system. The method may comprise controlling the magnetic resonance imaging system to perform an examination comprising multiple scans. The method may further comprise monitoring a sleep state of a patient on the basis of sensor data received from a patient state sensing system of the magnetic resonance imaging system. The method may further comprise dynamically determining at least part of a sequence in which the magnetic resonance imaging system is controlled to perform the scans. The determination may be made according to the monitored sleep state of the patient and according to a sleep-appropriateness score associated with one or more of the scans.

According to a third aspect, there is provided a computer program product comprising instructions which, when the program is executed by a computer, enable the computer to carry out the method of the second aspect.

According to a fourth aspect, there is provided a computer-readable medium having stored thereon the computer program product of the third aspect and/or computer-executable instructions which, when executed by a computer, enable the computer to carry out the method of the second aspect.

Optional features or sub-aspects described in relation to the first aspect apply as appropriate to any of the second-fourth aspects.

By "sleep state" may be meant a binary indication of whether the patient is asleep or awake or a state selected from a set comprising more than two states which additionally indicate the depth or phase of sleep, such as awake, REM-sleep, non-REM sleep, for example. "Sleep state" may also be understood as a patient measurement or a vector of patient measurements providing sufficient information to determine whether the patient is asleep, such as patient heart rate, breathing rate (both from a vital signs camera, for example), and normal camera vision.

By "scan" may be meant a single scan of a particular type undertaken for a single purpose as part of a larger "examination" comprising a number of such scans. Some examples of scans include a gradient echo scan, an echo-planar scan, a spin-echo scan, a diffusion scan. As used here, "sequence" thus refers not only to a plurality of such scans but also the order in which the scans are performed and "sequencing" may be construed accordingly.

Put another way, there is provided an MR scan scheduling system and method in which sleep habits and sleep state are determined, in which scheduling of the examination and of scans within the examination is adapted according to sleep habits, or in which scan parameters are adjusted according to sleep state, with the overall goal to improve image quality, shorten imaging times and decrease use of sedation.

These and other aspects of the invention will be apparent from and elucidated with reference to the following detailed description.

BRIEF DESCRIPTION OF THE DRAWINGS

Below, examples are described in more detail with reference to the attached drawings, in which.

DETAILED DESCRIPTION OF EMBODIMENTS

Figure 1:
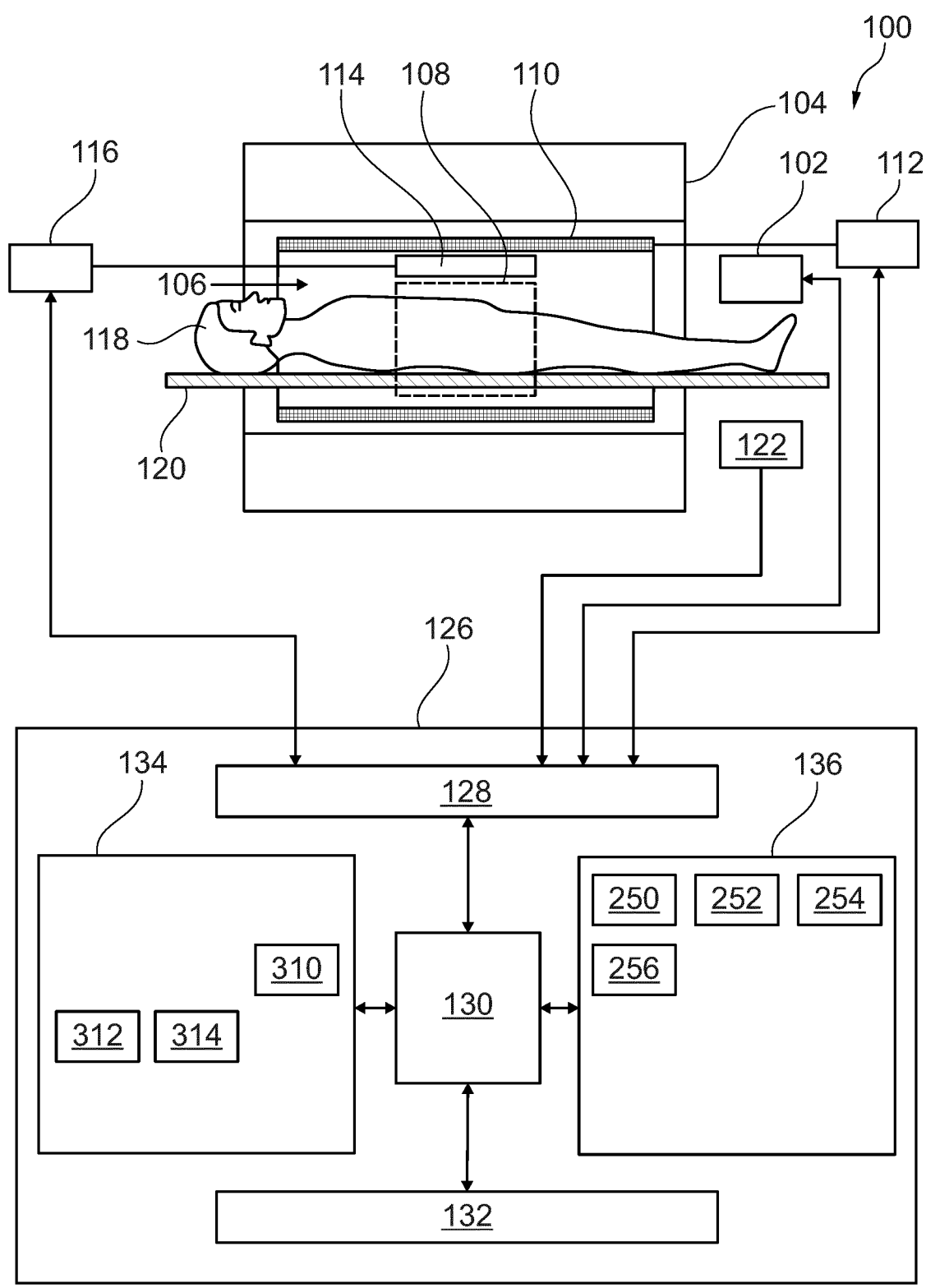
FIG. 1 illustrates a magnetic resonance imaging system including a control system.

FIG. 1 illustrates an exemplary magnetic resonance imaging system 100. The magnetic resonance imaging system 100 comprises a magnet 104 such as a superconducting cylindrical type magnet with a bore 106 through it that is large enough to receive a subject 118 on a support 120. Within the bore 106 of the cylindrical magnet 104 there is an imaging zone 108 where the magnetic field is strong and uniform enough to perform magnetic resonance imaging. Within the bore 106 there is also a set of magnetic field gradient coils 110 used for acquisition of magnetic resonance data to spatially encode magnetic spins within the imaging zone 108. The magnetic field gradient coils 110 contain three separate sets of coils for spatially encoding in three orthogonal spatial directions. The magnetic field gradient coils 110 are connected to a magnetic field gradient coil power supply 112 which supplies current to the magnetic field gradient coils 110. Adjacent to the imaging zone 108 is a radio-frequency antenna 114 for manipulating the orientations of magnetic spins within the imaging zone 108 and for receiving radio transmissions from spins also within the imaging zone 108. The radio frequency antenna 114 may contain multiple coil elements. The radio-frequency coil 114 is connected to a radio frequency transceiver 116. The radio-frequency antenna 114 and radio frequency transceiver 116 may be replaced by separate transmit and receive coils and a separate transmitter and receiver. It will be understood that the details of the magnetic resonance imaging system 100 are provided herein for the purposes of illustration only and that the techniques described herein are application to any MM system or to any other imaging system which is susceptible to imaging artifacts caused by patient motion. The magnetic resonance imaging system 100 further comprises a patient state sensing system 102 and optionally also an environmental control subsystem 122.

The magnetic field gradient coil power supply 112, the transceiver 116, the patient state sensing system 102, and the environmental control subsystem 122 are connected to a hardware interface 128 of a control system 126.

The control system 126 comprises a processor 130 connected to the hardware interface 128 along with a user interface 132, computer storage 134, and computer memory 136. The computer storage 134 contains, in use, sensor data 310 that was acquired using the patient state sensing system 102. The computer storage 134 optionally also contains in-bore lighting control data 312 and music/video data 314. The computer memory 136 contains a control module 250, a monitor module 252, a sequencing module 254, and optionally also an environmental control module 256. Each of the modules 250-256 contains computer-executable instructions.

The control module 250 contains computer-executable code which enables the processor 130 to control the operation and function of the magnetic resonance imaging system 100 in the manner described herein. In particular, the control module 250 is configured to control the magnetic resonance imaging system 100 to perform an examination comprising multiple scans. The control module 250 may be configured to adjust scan parameters during a said scan being performed by the magnetic resonance imaging system 100 according to the monitored sleep state.

The monitor module 252 is configured to monitor the sleep state of a patient on the basis of the sensor data 310 received from the patient state sensing system 102. In this example, the monitor module 252 is configured to detect, based on the sensor data 310, whether the patient is asleep (in a sleep state) or awake (in a non-sleep state). Sleep may be detected by methods such as camera-based measurements of heart rate and breathing rate and closed eye detection. The sensor data 310 received from the patient state sensing system 102 may thus comprise one or more (i) motion sensor data; (ii) patient heart rate data; (iii) patient breathing rate data; (iv) data indicating detection of patient closed eyes.

The sequencing module 254 is configured dynamically to determine at least part of a sequence in which the control module is to control the magnetic resonance imaging system to perform the scans. The determination is made according to the monitored sleep state of the patient and according to a sleep-appropriateness score associated with one or more of the scans. The sequencing module 254 may be configured to respond to the monitored sleep state of the patient indicating that the patient has entered the sleep state by prioritizing, as the next scan in the sequence, a first said scan having a first sleep-appropriateness score over a second said scan having a second sleep-appropriateness score, the first sleep-appropriateness score being higher than the second sleep-appropriateness score. Advantageously, more sleep-appropriate scans are thus prioritized to occur while the patient is asleep and other, less sleep appropriate scans, which therefore have a lower priority in terms of scheduling, may occur at any other time during the examination.

The sequencing module 254 may be configured to associate the one or more scans with the respective sleep-appropriateness scores using a rule-based scoring algorithm which takes as input one or more of the following parameters: (i) scan duration, (ii) scan noise level, (iii) scan type (relating to sensitivity to patient motion); (iv) level of patient interaction during the scan. The sleep-appropriateness score S may be defined as a sum of terms each comprising a weighting factor $w_i$ and a function $f_i(p)$ that depends on the parameter p. The factors $w_i$ may be adjusted empirically to set the relative weights of the parameters. The function may be any analytical function of the parameter p as a polynomial, exponential or other function. In case of scan duration, this function may simply be the identity function $f(p)=p$. In case of scan noise level, the function may be defined as $f(p)=-p^2$ because higher noise levels are increasingly inappropriate for sleep. The parameter scan type is introduced to the score to take into account the different sensitivities of various scan types to patient motion. More motion-sensitive scan types should deliver a high score, because they are more appropriate to be performed during sleep, and vice versa. Therefore the respective function may be a table of values each attributed to one of the scan types. For example, table values may be set for diffusion scans to 5, for all non-diffusion cartesian scans to 3, to non-diffusion radial and spiral scans to 1. The function for the parameter representing the level of patient interaction may also be implemented as a table. For example, scans requiring the patient to respond to requests as breath-hold commands may be assigned with the value −1, all other scans with 0.

The sequencing module 254 may be configured to prioritize sequencing of a said scan associated with a noise level that is lower than that associated with at least one other said scan to occur at or near the beginning of the sequence, to assist the patient in falling sleep. The scans may comprise at least one interactive scan involving a degree of patient interaction. The interactive scan may be associated with a requirement for one or more of patient repositioning and patient breath holding. In such a case, the sequencing module 254 may be further configured to prioritize sequencing of the interactive scan to occur at a point in the sequence at which the sleep state of the patient is determined to be awake. This may occur at or near the end of the scan, advantageously prevent interactive scans from hindering the patient in falling asleep. The sequencing module 254 may be configured to omit from the sequence a motion-tracking part of one or more subsequent scans in response to the monitored sleep state of the patient indicating that the patient has entered the sleep state. Motion tracking may form part of many motion-sensitive scans and typically makes them longer. Omitting motion tracking within these scans when the patient is detected to be asleep thus advantageously shortens the scans.

As mentioned above, the control module 250 may be configured to adjust scan parameters during a said scan being performed by the magnetic resonance imaging system 100 according to the monitored sleep state. Most MR scan types a tradeoff to be made between shorter imaging time with resulting lower sensitivity to motion artefacts at the cost of image quality or resolution. If a patient is detected to be awake, scan parameters may be adjusted by adjusting this tradeoff in the direction of a shorter and therefore less sensitive scan, whereas longer scan times with lower noise level may be chosen for patients that are currently asleep. The rule-based scoring algorithm as disclosed herein may be used to adjust scans to achieve this tradeoff, using for example an optimization algorithm. If a patient is currently asleep, then scan parameters may be iteratively adapted to increase a sleep-appropriateness score of the corresponding scan. If a patient is currently awake, then scan parameters may be iteratively adapted to decrease the sleep-appropriateness score. Any known optimization algorithm such as the steepest gradient-descent method may be used to perform this optimization. Optimization may be performed in a user-defined parameter space. For example, the parameter space for scan duration may be given by a maximal and a minimal scan duration that the optimization algorithm shall not exceed or fall below, respectively.

The environmental control module 256 may be configured to instruct the environmental control subsystem 122 to control an in-bore lighting condition to adopt a sleep-supporting state, for example on the basis of the in-bore lighting control data 312. The environmental control module 256 may be configured to instruct the environmental control subsystem 122 to play back music and/or video identified as being personal sleep triggers of the individual patient, this music and/or video having been prestored as the music/video data 314, for example.

Figure 2:
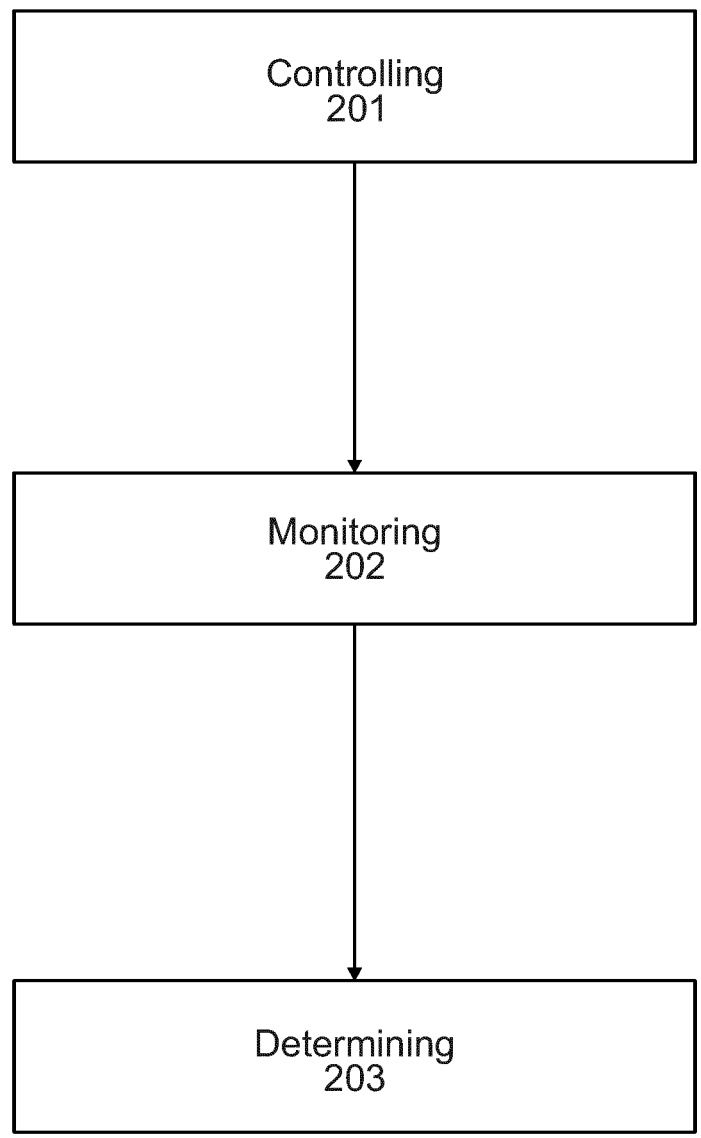
FIG. 2 represents a method performed by the control system of FIG. 1.

FIG. 2 illustrates a method performed by the control system 126 for controlling the magnetic resonance imaging system 100. The method comprises, at step 201, controlling (by the control module 250) the magnetic resonance imaging system 100 to perform an examination comprising multiple scans. The method further comprises, at step 202, monitoring (by the monitor module 252) a sleep state of a patient on the basis of the sensor data 310 received from the patient state sensing system 102 of the magnetic resonance imaging system 100. The method further comprises, at step 203, dynamically determining (by the sequencing module 254) at least part of a sequence in which the magnetic resonance imaging system 100 is controlled to perform the scans. The determination may be made according to the monitored sleep state of the patient and according to a sleep-appropriateness score associated with one or more of the scans.

One use case of the techniques described herein comprises one or more of the following approaches:
1. Identify potential sleepers and derive personal sleep habits and sleep triggers;
2. Coach patients to sleep during examination;
3. Schedule patients depending on sleep habits (time of day, scanner type);
4. Apply individual sleep triggers at the beginning of the examination;
5. Reschedule scans within the examination to support sleep;
6. Adjust scans depending on sleep state;
7. Adjust imaging environment to support sleep (adaptive lighting).

With reference to approach 1 ("Identify sleepers and derive personal sleep habits and sleep triggers"), potential sleepers may be identified based on an app-based questionnaire that includes questions such as:
"Can you fall asleep during driving or flying?"
"How much do you rate noise to disturb your sleep on a scale 1-5?"
"How long does it usually take you to fall asleep?"
"Which is your best sleeping posture?" (if not supine disqualifies as sleeper)
"Do you keep calm and confident in new situations? Rate on 1-5."
The app may also be used to produce some low level MR noise, aiding questions such as "You will hear similar sounds during your upcoming MR exam. Do you think you will be able to sleep in that exam, which will be beneficial for you and image quality?"

Each of these questions may be rated with a weight, and a pro-sleep answer adds the corresponding weight to an overall score. If the overall score exceeds a limit, the patient is identified as sleeper.

Criteria for the decision sleeper/non-sleeper (weights, overall limit) may be set heuristically when the product is launched and may be continuously refined during use of the product. Therefore, the pre-exam decision may be compared against data on the sleep status obtained during the actual exam for each patient. Criteria may then be updated such that the number of correct decisions over all patients is maximized. Correct here means that the patient fell asleep after the decision was taken that he is a sleeper.

If a patient qualifies as "sleeper" based on the current criteria, then sleep habits and sleep triggers may be derived from patient characteristics, personal device usage, and an extended questionnaire. An example for characteristics is that sleep times typically change with age, and depending on the age of a particular patient, this allows most likely sleep times. Times of personal device usage may also be evaluated to derive personal sleep times.

With reference to approach 2 ("Encourage and coach patient to sleep during exam"), information may again be supplied to the patient via an app on a personal device stating that sleep is helpful both for good image quality and patient experience. The app may be used to play MR noise so that the patient can accustom themselves to this sound. The sound may be played at low volume shortly after the patient falls asleep at home.

With reference to approach 3 ("Schedule patients depending on sleep habits and apply sleep triggers"), personal sleep habits may be used to schedule patients. "Night owls" are scheduled in the morning, "early birds" in the afternoon or evening. Non-sleepers are preferably scheduled on high field systems (e.g. 3T), where scans are generally shorter than on mid or low field systems and therefore less sensitive to motion artifacts. Personal sleep triggers may be applied at the beginning of the MR exam (personal piece of music or video, some personal belongings, usual evening drink e.g. night time tea and food).

With reference to approach 4 ("Reschedule scans within exam to induce or maintain sleep"), loud scans may be avoided at the beginning of the MR exam to allow the patient to fall asleep or during actual sleep to not wake the patient up. Loud scans may be rescheduled to the end of the exam to wake the patient up again. Similarly, any scans that require active patient interaction (breath-hold scans, repositioning, etc.) may be avoided at the beginning of the MR exam or during sleep.

With reference to approach 5 ("Reschedule motion sensitive scans within exam depending on sleep state"), this is based on the insight that MR scans have very different motion sensitivity. Longer scans, diffusion scans, and functional scans are examples with very high motion sensitivity. Such scans may be rescheduled to detected sleep phases.

With reference to approach 6 ("Adjust scans depending on sleep habit and sleep state"), most MR scan types allow a trade-off to be made between shorter imaging time with associated lower sensitivity to motion artifacts and image quality or resolution. For non-sleepers scans may be shortened, whereas longer scan times may be chosen for sleeping patients. Many scan types acquire additional MR data to track motion and discard affected MR image data (such as PROPELLER, RADIAL acquisitions, MR Navigators). The additional acquisition requires additional imaging time. The scan may be adjusted to avoid this additional acquisition during sleep phases of the patient, saving imaging time.

With reference to approach 7 ("Adjust imaging environment to support sleep"), room and in-bore lighting conditions may be adjusted to support sleep. Patient communication may be avoided if patient is asleep.

Aspects of the present invention may take the form of an entirely hardware embodiment, an entirely software embodiment (including firmware, resident software, micro-code, etc.) or an embodiment combining software and hardware aspects that may all generally be referred to herein as a "module" or "system". Furthermore, aspects of the present invention may take the form of a computer program product embodied in one or more computer readable medium(s) having computer executable code embodied thereon. Any combination of one or more computer readable medium(s) may be utilized. The computer readable medium may be a computer readable signal medium or a computer readable storage medium. A "computer-readable storage medium" as used herein encompasses any tangible storage medium which may store instructions which are executable by a processor of a computing device. The computer-readable storage medium may be referred to as a non-transitory computer-readable storage medium. "Computer memory" or "memory" is an example of a computer-readable storage medium. Computer memory is any memory which is directly accessible to a processor. "Computer storage" or "storage" is a further example of a computer-readable storage medium. Computer storage is any non-volatile computer-readable storage medium. In some embodiments computer storage may also be computer memory or vice versa.

A "processor" as used herein encompasses an electronic component which is able to execute a program or machine executable instruction or computer executable code. References to the computing device comprising "a processor" should be interpreted as possibly containing more than one processor or processing core.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

LIST OF REFERENCE SIGNS 100 magnetic resonance imaging system
102 patient state sensing system
104 magnet
106 bore
108 imaging zone
110 magnetic field gradient coils
112 magnetic field gradient coil power supply
114 radio-frequency antenna
116 radio frequency transceiver
118 subject
120 support
122 environmental control subsystem
126 control system
128 hardware interface
130 processor
132 user interface
134 computer storage
136 computer memory
201-203 method steps
250 control module
252 monitor module
254 sequencing module
256 environmental control module
310 sensor data
312-314 other data

The invention claimed is:

1. A control system for a magnetic resonance imaging system, the control system comprising:
   a control module configured to control the magnetic resonance imaging system to perform an examination comprising multiple scans;
   a monitor module configured to monitor a sleep state of a patient on the basis of sensor data received from a patient state sensing system of the magnetic resonance imaging system; and
   a sequencing module configured dynamically to determine at least part of a sequence in which the control module is to control the magnetic resonance imaging system to perform the scans, the determination being made according to the monitored sleep state of the patient and according to a sleep-appropriateness score associated with one or more of the scans.

2. The control system of claim 1, wherein the sequencing module is configured to respond to the monitored sleep state of the patient indicating that the patient has entered the sleep state by prioritizing, as the next scan in the sequence, a first said scan having a first sleep-appropriateness score over a second said scan having a second sleep-appropriateness score, the first sleep-appropriateness score being higher than the second sleep-appropriateness score.

3. The control system of claim 1, wherein the sequencing module is configured to associate the one or more scans with the respective sleep-appropriateness scores using a rule-based scoring algorithm which takes as input one or more of the following parameters: (i) scan duration, (ii) scan noise level, (iii) scan type (relating to sensitivity to patient motion); (iv) level of patient interaction during the scan.

4. The control system of claim 3, wherein the rule-based scoring algorithm determines the sleep-appropriateness score S for a respective said scan based on a sum of terms each comprising a weighting factor $w_i$ and a function $f_i(p)$ that depends on the parameter p.

5. The control system of claim 4, wherein the function for a said term taking scan duration as the input parameter p is defined as $f(p)=p$.

6. The control system of claim 4, wherein the function for a said term taking scan noise level as the input parameter p is be defined as $f(p)=-p^2$.

7. The control system of claim 4, wherein the function for a said term taking scan type or level of patient interaction as the input parameter p is defined as a table of values each attributed to one of the said scan types or levels of patient interaction, respectively.

8. The control system of claim 1, wherein the control module is configured to adjust scan parameters during a said scan being performed by the magnetic resonance imaging system according to the monitored sleep state.

9. The control system of claim 8, wherein the control module is configured to adjust the scan parameters by decreasing scan duration when the patient is detected to be awake and/or by increasing scan duration when the patient is detected to be asleep.

10. The control system of claim 1, wherein the sequencing module is configured to omit from the sequence a motion-tracking part of one or more subsequent scans in response to the monitored sleep state of the patient indicating that the patient has entered the sleep state.

11. The control system of claim 1, wherein the sensor data received from the patient state sensing system of the magnetic resonance imaging system comprises one or more (i) motion sensor data; (ii) patient heart rate data; (iii) patient breathing rate data; (iv) data indicating detection of patient closed eyes.

12. The control system of claim 1, further comprising an environmental control module configured to instruct an environmental control subsystem of the magnetic resonance imaging system to control an in-bore lighting condition to adopt a sleep-supporting state.

13. The control system of claim 1, further comprising an environmental control module configured to instruct an environmental control subsystem of the magnetic resonance imaging system to play back music and/or video identified as being personal sleep triggers of the individual patient.

14. A magnetic resonance imaging system comprising the control system of claim 1.

15. A computer-implemented method of controlling a magnetic resonance imaging system, the method comprising:
controlling the magnetic resonance imaging system to perform an examination comprising multiple scans;
monitoring a sleep state of a patient on the basis of sensor data received from a patient state sensing system of the magnetic resonance imaging system; and
dynamically determining at least part of a sequence in which the magnetic resonance imaging system is controlled to perform the scans, the determination being made according to the monitored sleep state of the patient and according to a sleep-appropriateness score associated with one or more of the scans.

16. A computer-readable medium having stored thereon computer-executable instructions which, when executed by a computer, enable the computer to carry out the method of claim 15.

* * * * *